(12) United States Patent
Deckmyn et al.

(10) Patent No.: US 7,754,215 B2
(45) Date of Patent: Jul. 13, 2010

(54) ANTITHROMBOTIC THERAPY WITH ANTIBODIES BINDING TO THE A3 DOMAIN OF VON WILLEBRAND FACTOR (VWF)

(75) Inventors: Hans Deckmyn, Linden (BE); Nancy Cauwenberghs, Londerzeel (BE); Karen Vanhoorelbeke, Zwevegem (BE)

(73) Assignee: K.U. Leuven Research & Development, Leuven (BE)

( * ) Notice: Subject to any disclaimer, the term of this patent is extended or adjusted under 35 U.S.C. 154(b) by 546 days.

(21) Appl. No.: 11/612,257

(22) Filed: Dec. 18, 2006

(65) Prior Publication Data

US 2007/0081999 A1    Apr. 12, 2007

Related U.S. Application Data

(63) Continuation of application No. 10/450,740, filed as application No. PCT/BE01/00220 on Dec. 21, 2001, now abandoned.

(30) Foreign Application Priority Data

Dec. 22, 2000    (GB) ................... 0031448.4

(51) Int. Cl.
*A61K 39/395* (2006.01)
(52) U.S. Cl. .............. 424/145.1; 424/133.1; 424/139.1; 530/387.3; 530/387.9; 530/388.1; 530/388.25
(58) Field of Classification Search ....................... None
See application file for complete search history.

(56) References Cited

U.S. PATENT DOCUMENTS

| | | | |
|---|---|---|---|
| 5,238,919 | A | 8/1993 | Zimmerman et al. |
| 5,609,869 | A | 3/1997 | Quertermous et al. |
| 5,710,131 | A | 1/1998 | Hemberger et al. |
| 5,837,488 | A | 11/1998 | Garfinkel et al. |
| 5,900,476 | A | 5/1999 | Ruggeri et al. |
| 6,228,360 | B1 * | 5/2001 | Co et al. .............. 424/145.1 |
| 6,251,393 | B1 * | 6/2001 | Handin et al. .......... 424/135.1 |

FOREIGN PATENT DOCUMENTS

| | | |
|---|---|---|
| EP | 0 255 206 A2 | 5/1987 |
| WO | WO 95/01375 | 1/1995 |

OTHER PUBLICATIONS

Fressinaud et al. (J Lab Clin Med 1988, 112:58-67).*
Hoylaerts MF (Verh K Acad Geneeskd Belg. 1997;59(3):161-83).*
Alevriadou et al. (Blood. Mar. 1, 1993;81(5):1263-76).*
Depraetere et al., "Epitope Mapping of a Monoclonal Antibody that Inhibits vWF Interaction with Collagen," *Haemostasis* 30:84 (2000) (Abstract).
Hoylaerts et al., "von Willebrand Factor Binds to Native Collagen VI Primarily Via its A1 Domain," *Biochem. J.* 324:185-191 (1997).
Mohri et al., "Autoantibody Inhibits Binding of von Willebrand Factor to Glycoprotein lb and Collagen in Multiple Myeloma: Recognition Sites Present on the A1 loop and A3 Domains of von Willebrand Factor," *Bood Coagulation and Fibrinolysis* 9:91-97 (1998).
Obert et al., "Conformational Changes in the A3 Domain of von Willebrand Factor Modulate the Interaction of the A1 Domain With Platelet Glycoprotein lb," *Blood* 93:1959-1968 (1999).
Schaffer et al., "Recombinant Leech Antiplatelet Protein Prevents Collagen-Mediated Platelet Aggregation But Not Collagen Graft Thombosis in Baboons," *Arterioscler Thromb.* 13:1593-601 (1993).
Tangelder et al., "Wall Shear Rate in Arterioles in vivo: Least Estimates From Platelet Velocity Profiles," *Am J Physiol.* 254:H1059-64 (1988).
Verkleij et al;, "Adhesive Domains in the Collagen III Fragment α1 (III)CB4 that Support α2β1-and von Willebrand Factor-mediated Platelet Adhesion under Flow Conditions," *Thrombosis and Haemostasis* 82:1137-1144 (1999).

* cited by examiner

*Primary Examiner*—Michael Szperka
(74) *Attorney, Agent, or Firm*—Clark & Elbing LLP

(57) ABSTRACT

The present invention clearly demonstrates that vWF-collagen interaction, via the A3 domain of vWF, plays an important role in acute platelet-dependent arterial thrombus formation and that blocking the A3 domain in a vWF-collagen interaction can induce complete abolition of thrombus formation in the injured and stenosed baboon femoral arteries. Accordingly, an antibody or an antigen recognizing fragment thereof binding specifically to the A3 domain of vWF or an epitope thereof can be used for the prevention of acute arterial thrombotic syndromes or to manufacture medicines to for the prevention of acute arterial thrombotic syndromes.

21 Claims, 11 Drawing Sheets

A

B shear s$^{-1}$

Figure 1:
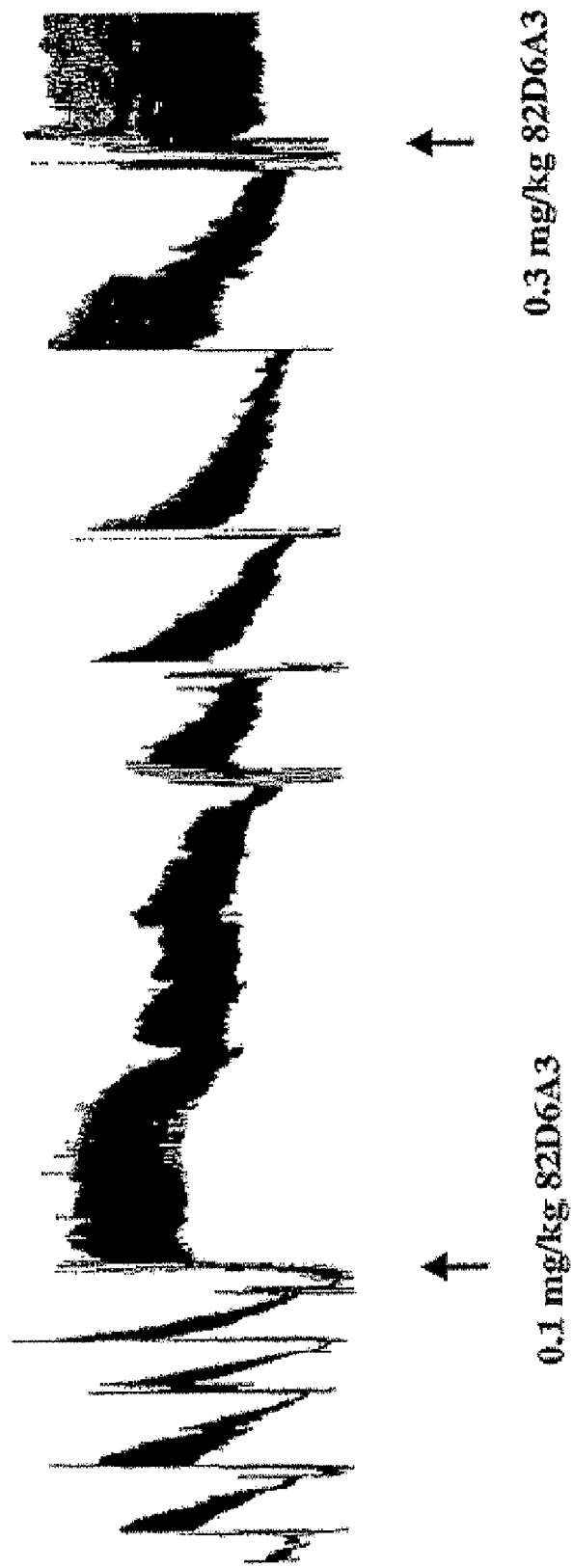

```
SITTIDVPWNVVPEK    vWF(974-989)
   :   | |  |
   FLNSPWRV        L15G8 phage
        | | | |
     XXSPWR        C6 phages
```

Figure 11

ANTITHROMBOTIC THERAPY WITH ANTIBODIES BINDING TO THE A3 DOMAIN OF VON WILLEBRAND FACTOR (VWF)

CROSS REFERENCE TO RELATED APPLICATIONS

This application is a continuation of U.S. Ser. No. 10/450,740, which is the U.S. National Stage of International Application No. PCT/BE01/00220, filed Dec. 21, 2001, which was published in English under PCT Article 21(2). PCT/BE01/00200 also claims benefit of British Patent Application No. 0031448.4 filed Dec. 22, 2000.

BACKGROUND OF THE INVENTION

Damage of an arterial vessel wall leads to platelet adhesion, aggregation and ultimately may result in thrombosis. These events are known to contribute to the development of occlusive syndromes in the coronary, cerebral and peripheral vascular system, as well as restenosis and intimal hyperplasia that occur after angioplasty, atherectomy and arterial stenting (1;2). In both thrombosis and reocclusion, platelets adhere to the subendothelium of damaged blood vessels through an interaction with von Willebrand factor (vWF) that forms a bridge between collagen, a component of the damaged vessel wall and the platelet glycoprotein Ib (GPIb) (3). This reversible adhesion or tethering of the platelets at high shear rate is followed by a firm adhesion through the collagen receptors (GPIa-IIa; GWPIV, ... )(4) resulting in platelet activation and release of ADP, thromboxane, and serotonin. These in turn activate additional platelets and trigger the conformational activation of the platelet GPIIb/IIIa receptor, leading to fibrinogen binding and finally to platelet aggregation (5). Ultimately, a platelet-initiated thrombus is formed.

The search for anti-platelet drugs in the prevention of thrombosis has recently focused on the blockade of the GPIIb-IIIa receptor and on the inhibition of the vWF-GPIb axis. The best characterized drugs are antibodies and peptides that block the binding of adhesive proteins to GPIIb-IIIa which have been tested in animal models and of which many are being tested in clinical trials and/or are used in the clinic (6-8). Also compounds that interfere with the vWF-GPIb axis inhibit thrombus formation in various animal models. The GPIb/IX/V complex consists of 4 different polypeptides GPIbα, GPIbβ, GPIX and GPV which are all members of the leucine-rich protein family (9; 10). The N-terminal domain of the GPIbα polypeptide contains the vWF binding site (11). vWF is composed of several homologous domains each covering different functions: it interacts through its A1 domain mainly with the GPIb/V/IX complex (12), whereas its A3 domain predominantly interacts with fibrillar collagen fibers (13; 14). Compounds that interact with GPIbα, like the GPIb-binding snake venom proteins echicetin and crotalin (15; 16), an anti-guinea pig GPIb antibody (17; 18), a recombinant A1 domain fragment (VCL) (2;23) and recently an anti-human GPIb antibody (19) or compounds that bind to vWF like anti-A1-vWF-monoclonal antibodies (mAbs) (20; 21), aurin tricarboxylic acid (ATA) (22) are inhibiting in vivo thrombus formation.

Specific blockade of the vWF-collagen interaction in vivo has not yet been demonstrated but could be a novel strategy for the prevention of thrombus formation in stenosed arteries. We here describe for the first time the antithrombotic effect of a murine anti-human vWF mAb82D6A3, known to bind to the A3-domain and to inhibit vWF binding to fibrillar collagens type I, III and calf's skin collagen but not to collagen VI (24), Vanhoorelbeke et al., 2000b).

The present study aimed to evaluate the antithrombotic efficacy of mAb 82D6A3 in baboons by using a modified Folts' model, where cyclic flow reductions (CFRs) due to thrombus formation and its dislodgment are measured in an artery following intimal damage and placement of a critical stenosis to reduce the lumen diameter (25).

SUMMARY OF THE INVENTION

The present invention provides ligands for use as a medicaments which specifically recognises domain A3 of von Willebrand factor or an epitope of the A3 domain of von Willebrand factor. The ligands of the invention inhibit interaction of von Willebrand factor with collagen, more particularly fibrillar collagen fibers and/or thrombogenic collagen which is exposed in a damaged blood vessel wall, such as type I and type III collagen.

According to a particular embodiment of the invention, the ligands used in the methods of treatment of the invention are do not directly block the GPIb-vWF axis or the GPIIb-IIIa receptor.

Specific embodiments of the ligands used as medicaments in the context of the present invention are ligands that are antibodies, more specifically antibodies against the A3 domain of von Willebrand factor or a fragment thereof. More particularly, the ligands are monoclonal antibodies or a fragment, such as an Fab, Fab' or F (ab') 2 thereof, or homologues of such fragments, which specifically bind to the A3 domain of von Willebrand factor or a fragment thereof. Optionally, the antibodies used as medicaments in the methods of treatment of the present invention are humanized antibodies, such as antibodies having only the hypervariable regions of non-human, animal, e.g. rodent, origin. A more specific embodiment of the present invention relates to the use as a medicament for therapy or prevention of a monoclonal antibody or antigen binding fragment thereof, which monoclonal antibody has a reactivity substantially identical to the monoclonal antibody obtained from a cell line, that has been deposited with the Belgian Collections of Micro-organisms, under accession number LMBP 5606CB.

The ligands used as medicaments in the context of the present invention optionally have one or more, preferably all of the features described hereafter. The ligand does not induce severe decline of circulating vWF-levels or a severe decline in platelet count when administered to a primate by bolus intravenous administration at a dose up to 600 µg/kg; the ligand does not result in severe prolongation of bleeding time or does not induce thrombocytopenia when administered to a primate by bolus intravenous administration at a dose up to 600 µg/kg; the ligand occupies vWF and inhibits vWF-collagen binding when administered at a therapeutically effective dose up to 600 µg/kg to a primate by bolus intravenous administration; the ligand does not induce severe decline of circulating vWF-levels; the ligand does not drastically affect clotting time (Prothrombin Time (PT) or activated Partial Thromboplastin Time (aPTT)); the ligand, by interfering with the vWF-collagen interaction, inhibits platelet tethering to a blood vessel surface under high shear stress or at high shear rates.

A further aspect of the invention provides methods of treating a thrombotic disorder in an individual in need thereof using the ligands described herein. Thus, the methods of use described for the ligands of the present invention are methods of antithrombotic treatment. Indeed, the ligands described above are disclosed to interfere with the vWF-collagen interaction and thereby inhibit the first steps of thrombus formation in an individual. Additionally, by interfering with the vWF-collagen interaction, the ligands of the present invention block the first steps of thrombus formation before platelet activation and platelet secretion of vasoactive compounds that induce smooth muscle cell migration and proliferation resulting in restenosis. Particularly the use of the ligands of the invention is based on the fact that, by interfering with the vWF-collagen interaction under high shear stress in an individual, the ligands of the invention inhibit platelet tethering to a damaged blood vessel surface.

Thus the ligands of the present invention are presented to be useful in an antithrombotic treatment to prevent the formation of thrombus, which can be either a non-occlusive thrombus or an occlusive thrombus. Particularly, the antithrombotic treatment is envisaged to prevent arterial thrombus formation, such as acute coronary occlusion. The ligands of the invention are further provided in a method of anti-thrombotic treatment to maintain the patency of diseased arteries, to prevent restenosis, such as after PCTA or stenting, to prevent thrombus formation in stenosed arteries, to prevent hyperplasia after angioplasty, atherectomy or arterial stenting, to prevent unstable angina, and generally to prevent or treat the occlusive syndrome in a vascular system.

According to a particular embodiment of the invention, the ligand is administered as an immunoconjugate with a thrombolytic agent.

More particularly, the immunoconjugate contains a thrombolytic agent or a recombinant variant or fragment thereof which is selected from the group consisting of staphylokinase, tissue plasminogen activator, streptokinase, single chain streptokinase, urokinase and acyl plasminogen-streptokinase complex.

According to particular embodiments, the present invention thus provides antithrombotic agents which bind with the A3 domain of von Willebrand factor or an epitope thereof, resulting in the inhibition of interaction of von Willebrand factor with collagen, but which is characterized by one or more of the following advantages: administration to an individual does not induce severe bleeding disorders at a minimal medicinal effective dose to exhibit antithrombotic action, does not induce severe decline of circulating vWF-levels or a severe decline in platelet count at a minimal medicinal effective dose to exhibit antithrombotic action, does not result in severe prolongation of bleeding time or does not induce thrombocytopenia at a minimal medicinal effective dose to exhibit antithrombotic action, and/or does not drastically affect clotting time (Prothrombin Time (PT) or activated Partial Thromboplastin Time (aPTT)) at a minimal medicinal effective dose to exhibit antithrombotic action. The invention provides methods of antithrombotic therapy in an individual, comprising administering to the individual at risk of thrombosis, a therapeutically effective amount of the antithrombotic agents of the present invention which inhibits the binding of von Willebrand factor to collagen of a damage blood vessel wall and thereby inhibits platelet tethering to a damaged blood vessel surface.

The invention further provides pharmaceutical compositions, comprising the ligands described herein, in admixture with a pharmaceutically acceptable carrier.

The pharmaceutical compositions for use in the methods described herein optionally further comprise a thrombolytic agent in a form either for simultaneous or sequential use.

Yet another aspect of the present invention provides methods for screening and selecting a medicinal effective and acceptable antithrombotic agent which inhibits von Willebrand collagen binding comprising: a) characterising agents which inhibit von Willebrand collagen binding. b) administering said agent to a mammal and preferably to a primate with injured blood vessel. c) selecting the agents which at a dosis that significantly reduces cyclic flow reductions (CFR) do not drastically affect platelet count, do not drastically increase bleeding time, do not drastically change clotting time as measured by an assay such as activated Partial Tbromboplastin Time or Prothrombin Time and do not drastically affect circulating vWF levels.

Yet another aspect of the invention provides polynucleotides encoding for the antigen binding Fab, Fab' or F (ab') 2 fragment of the ligands of the present invention, capable of binding tot the A3 domain of vWF.

Yet another aspect of the invention provides a DNA probe for detecting the polynucleotide sequence encoding the antigen binding Fab, Fab' or F (ab') 2 fragment of the ligands of the present invention, comprising a nucleic acid molecule having a sequence complementary to the coding sequence of the polynucleotides encoding the antigen binding fragments of the ligands of the present invention.

ILLUSTRATIVE EMBODIMENTS OF THE INVENTION

Examples

Materials

Human placental collagen type I and III and calfskin type I were purchased from Sigma (St. Louis, Mo.). The collagens were solubilized in 50 mmol/L acetic acid and subsequently dialyzed against phosphate-buffered saline PBS (48 hours, 4° C.) to obtain fibrillar collagen. The phage display library with the random hexapeptides flanked by cysteine residues was obtained from Corvas (Gent, Belgium), the pentadecamer phage display peptide library was a kind gift of Dr. G. Smith (University of Missouri, Colombia, Mo.). vWF was purchased from the Red Cross (Belgium). The SpI proteolytic fragment and recombinant A3-domain were kind gifts of Drs. JS Girma (INSERM 134, Paris) and Ph. G. de Groot (Utrecht, The Netherlands).

Purification of mAb 82D6A3 mAb 82D6A3 was obtained from a cell line, that has been deposited with the Belgian Collections of Micro-organisms, under accession number LMBP 5606CB and was purified from ascites by protein A chromatography.

Preparation of 82D6A3 F(ab) Fragment.

82D6A3-F(ab) was prepared by digestion with papain. Briefly, 5 mg Ab was digested with 50 µg papain (Sigma) in the presence of 10 mmol/L cysteine and 50 mmol/L EDTA (37° C., overnight). The F(ab) was purified by protein A affinity chromatography (Pharmacia, Roosendaal, The Netherlands) and purity was checked by SDS-PAGE.

Surgical Preparation

Seven baboons of either sex, weighing 12-18 kg were used in the present study.

The experimental procedure followed was a modification of the original Folts' model (25). Baboons were anaesthetized with ketamine hydrochloride (10 mg/kg, i.m.), intubated with a cuffed endotracheal tube and ventilated by a respirator with oxygen supplemented with 0.5% Fluothane to maintain anaesthesia. Body temperature was maintained at 37° C. with a heating table. A catheter was placed in a femoral vein for drug administration and blood sampling. A segment of another femoral artery was gently dissected free from surrounding tissue and a perivascular ultrasonic flow probe (Transonic Systems Inc., New York, N.Y.) was placed around the distal dissection site. The mean and phasic blood flow were recorded continuously throughout the experiment. Baboons were allowed to stabilize for 30 min. Then the proximal dissection site of the femoral artery was injured by applying 3 occlusions of the artery for ten seconds with 2 mm interval using a spring-loaded forceps. A spring-loaded clamp next was placed in the middle of the injured site to produce an external stenosis of 65-80%. A gradual decline in blood flow due to platelet adhesion and aggregation was observed. When flow reached zero, blood flow was restored by pushing the spring of the clamp to mechanically dislodge the platelet-rich thrombus. This repetitive pattern of decreasing blood flow following mechanically restoration was referred to as cyclic flow reductions (CFRs). Additional endothelial injury and appropriate external stenosis selection was repeated. Finally, stable CFRs were obtained in these baboons. After a 60-minute control period of reproducible CFRs (t=−60 min to 0 min), test agents (saline or mAb 82D6A3) were given via an intravenous bolus injection (t=0) and monitoring was continued up to 60 minutes after drug administration (t=+60 min). The antithrombotic effect was quantified by comparing the number of CFRs per hour before and after drug administration. Blood samples for the different laboratory measurements (platelet count, coagulation, vWF occupation, vWF-collagen binding and plasma levels) were drawn at t=0, +30, +60, +150, +300 min and 24, 48 hours after treatment.

Drug treatment: The doses of mAb 82D6A3 were selected on the base of preliminary dose-finding studies. In group I, two baboons were used as saline control. Three baboons, group II, received a dose of 0.1 mg/kg mAb 82D6A3, after 60 min recording, an additional 0.2 mg/kg mAb 82D6A3 was given. Since a preliminary study showed that mAb 82D6A3 has a long halflife, this therefore resulted in a final dose of 0.3 mg/kg. In group III, a dose of 0.6 mg/kg mAb 82D6A3 was given to two baboons. All agents were diluted with saline.

Platelet Count, Coagulation and Bleeding Time

All blood samples were collected into a plastic syringe containing a final concentration of 0.32% trisodium citrate. The platelet count was determined using a Technicon $H_2$ blood cell analyzer (Bayer Diagnostics, Tarrytown, N.Y.).

Prothrombin time (PT) and activated partial thromboplastin time (aPTT) were measured at 37° C. using a coagulometer (Clotex II, Hyland).

The template bleeding time was measured at the surface of the forearm using the Simplate® II device (Organon Teknika, Durham, N.C.). The volar surface of the forearm was shaved, and a pressure cuff was applied and inflated to 40 mmHg. Time elapsed until the visual cessation of blood onto the filter paper was recorded as the bleeding time. Bleeding times were followed for up to ten minutes.

Plasma Concentration of 82D6A3

Microtiter plates (96-well, Greiner, Frickenhausen, Germany) were coated overnight at 4° C. with 5 μg/ml (in PBS, 100 μl/well) goat anti-mouse IgG whole molecule (Sigma, St. Louis, Mo.). Plates were blocked with 3% milk powder (PBS, 250 μl/well) for 2 hours at room temperature (RT). Frozen plasma samples were thawed and incubated for 5 min at 37° C. before addition to the plate. Dilution series of the samples ($\frac{1}{2}$ in PBS) were made and incubated for 2 hours at RT. Goat anti-mouse IgG labelled with horse radish peroxidase (HRP) were added and were incubated for 1 hour at RT. Visualization was obtained with ortho-phenylenediamine (OPD, Sigma) and the colouring reaction was stopped with 4 mol/l $H_2SO_4$. The absorbance was determined at 490 nm. After each incubation step, plates were washed with PBS, 0.1% Tween-20, three times after coating and blocking steps and twelve times elsewhere. The plasma concentration of mAb 82D6A3 in each sample was calculated from a standard curve. This curve was obtained by adding known amounts of mAb 82D6A3 to baboon plasma (free of antibody) and plating $\frac{1}{2}$ dilutions in PUS (starting from 6 μg/ml).

VWF-Ag Levels

Determination of the vWF-Ag levels was performed essentially as described (26). Briefly, microtiter plates were coated with a polyclonal anti-vWT-Ig-solution (Dako, Glostrup, Denmark). Plates were blocked with 3% milkpowder and samples were added to the wells at $\frac{1}{40}$ to $\frac{1}{2560}$ dilutions (samples were diluted in PBS, 0.3% milkpowder). Bound vWF was detected with rabbit anti-human vWF HRP antibodies (Dako). Visualization and wash steps were performed as described above. vWF-Ag levels were calculated from a standard curve obtained by adding $\frac{1}{40}$ to $\frac{1}{2560}$ dilutions to the coated wells of a human plasma pool, known to contain 10 μg/ml human vWF.

vWF Occupancy

Microtiter plates (96-well) were coated overnight at 4° C. with 125 μl/well of a polyclonal anti-vWF-Ig-solution (Dako) ($\frac{1}{1000}$ in PBS). Plates were blocked with 3% milk powder solution (in PBS, 250 μl/well) for 2 hours at room temperature (RT). Plasma samples were incubated for 5 min at 37° C. before addition to the plate. Pure samples were added and dilution series ($\frac{1}{2}$ in PBS) were made. Samples were incubated for 2 hours at RT. Samples containing 100% occupied vWF were obtained by adding a saturating amount of mAb 82D6A3 (6 μg/ml) to the corresponding baboon plasma. Bound mAb 82D6A3 was detected by addition of goat anti-mouse Ig-HRP (1 hour at RT). Visualization and wash steps were performed as described above. The vWF-occupancy of each sample was calculated as follows: (A490 nm sample/ A490 nm sample saturated with mAb 82D6A3)*100.

Determination of the vWF-Collagen Binding Activity

The ELISA was performed essentially as described (26). Briefly, microtiter plates were coated with human collagen type I (Sigma). Plates were blocked with 3% milk powder solution (in PBS, 250 μl/well). Pure sample and $\frac{1}{2}$ dilution series were added. Bound vWF was detected with rabbit anti-human vWF-HRP antibodies. Binding of baboon vWF to collagen in the different blood samples was compared to the binding of vWF in the blood sample taken at time zero (pre sample) which was set as 100%.

Determination of vWF Binding to Collagen and Inhibition by F(ab) Fragment of 82D6A3.

A 96-well plate was coated overnight with human collagen type I or III or calfskin collagen type I (25 μg/ml) and blocked. 2.5 μg/ml of recombinant vWF was used in the binding experiments. For the competition experiments, purified human vWF (0.5 μg/ml fc) or plasma ($\frac{1}{50}$ fc) was preincubated with a dilution series of 82D6A3 or its F(ab) fragment during 30 min in a preblocked 96-well plate. Then the mixtures were added to the blocked collagen-coated plate. After 90 min incubation bound vWF was detected with a polygonal anti-vWF-HRP conjugated antibody (Dako, Glostrup, Denmark) and visualization was performed with orthophenylenediamine (OPD, Sigma). The reaction was stopped with 4mol/L $H_2SO_4$ and absorbance was determined at 490-630 nm.

In between each incubation step the plates were washed 3-9 times with PBS (0.1% Tween 20).

Flow Experiments.

Plastic thermanox coverslips were rinsed with 40% ethanol and washed with water before spraying with human fibrillar collagen type I (100 µl (1 mg/ml)/coverslip). Blood was taken from healthy volunteers who had not taken aspirin or analogues for the last 10 days. The blood was anticoagulated with 25 U/ml low molecular weight heparin (LMWH) (Leo Pharmaceuticals, Vilvoorde, Belgium). The perfusion experiments were performed in a Sakariassen type flow chamber at 37° C., at wall shear rates of 600 s$^{-1}$, 1300 s$^{-1}$ and 2600 s$^{-1}$. The perfusion chamber and tubings were rinsed with plasma during 20 min, and washed with 25 ml Hepes buffered saline (HBS) before starting the experiment. In each experiment 15 ml blood, preincubated for 15 min with an inhibitor as indicated, was perfused for 5 min. After the perfusion, coverslips were rinsed with 25 ml Hepes buffered saline and put in 0.5% glutardialdehyde (10 min). Next the coverslips were placed in methanol (5 mm), stained with May-Grünwald (3-5 min) and Giemsa (15-20 min) and washed 2 times with destined water. Coverslips were dried and analysed with an image analyser as described (29).

Isolation MoAb Binding Phages.

Selection of phages was performed as follows. Biotinylated (see below) MoAb (10 µg) was bound to blocked streptavidin-coated magnetic beads (Dynal, Oslo, Norway). $2.10^{12}$ phages (PBS, 0.2% milkpowder) were first incubated with blocked streptavidine-coated beads for 1 hour to eliminate the streptavidin-binders. Next the phages were added to the MoAb containing beads and after 90 min the input phages were removed and the beads were washed 10 times with PBS (0.1% Tween-20) to remove the non-specific binders. The bound phages were eluted with 0.1 mol/L glycine, pH 2.2, and the eluate was immediately neutralized with 1 mol/L Tris, pH 8. After amplification of the phages, additional rounds of panning were performed. Phages were amplified by infection of *Escherichia coli* TG1 cells and partially purified from the supernatant by polyethylene glycol precipitation. Individual phage bearing *E. coli* were grown in a 96-well plate, and the supernatant was tested for the presence of 82D6A3-binding phages. Phage DNA was prepared and sequencing reactions were performed according to the T7-polymerase sequencing kit (Pharmacia) using the primer 5'-TGAATTTTCTGTAT-GAGG-3' (Seq. Id. 1).

Measurement of phage binding to 82D6A3. A 96-well plate was coated overnight with purified 82D6A3 (10 µg/mL). After 2 hours blocking with 2% milkpowder, a dilution series of the individual phage clones in PBS with 0.2% milkpowder was added to the wells and phages were incubated at room temperature for 90 min. Bound phages were detected after a 1-hour incubation with a polyclonal anti-M13-HBP conjugated antibody (Pharmacia) and visualization was performed with OPD.

Specificity of Phage Binding to 82D6A3.

A 96-well plate was coated overnight with purified 82D6A3 (10 µg/ml). After 2 hours blocking with 2% milkpowder a dilution series of vWF or recombinant A3 domain was added. After a 30 min preincubation, a constant amount of phages was added to the vWF/A3 containing wells. 90 min later bound phages were detected as described above. Competition between different phage clones for binding to 82D6A3 was analysed as above, except that $2.10^{10}$/ml biotinylated phages of clone 1 were mixed with various concentrations of phages from clone 2, after which bound biotinylated phages were detected with streptavidin-HRP and OPD.

MoAb and phages were biotinylated using NHS-LC-Biotin (Pierce, Rockford, Ill.) according to the manufacturer's instructions.

Immunoblotting of Phages

Purified phage clones ($2.10^{10}$) were electrophoresed on a 10% SDS-PAGE gel under reducing and non-reducing conditions and electroblotted to a nitrocellulose membrane. After blocking the membrane with 4% skimmed milk in PBS, the membrane was incubated with 82D6A3 (2 µg/ml) during 90 min, followed by a 1 hour incubation with GaM-FR and developed using the ECL detection system from Amersham (Buckinghamshire, England). After each incubation step the membrane was washed with PBS containing 0.05% Tween80.

Results

Antithrombotic Effect

Figure 2:
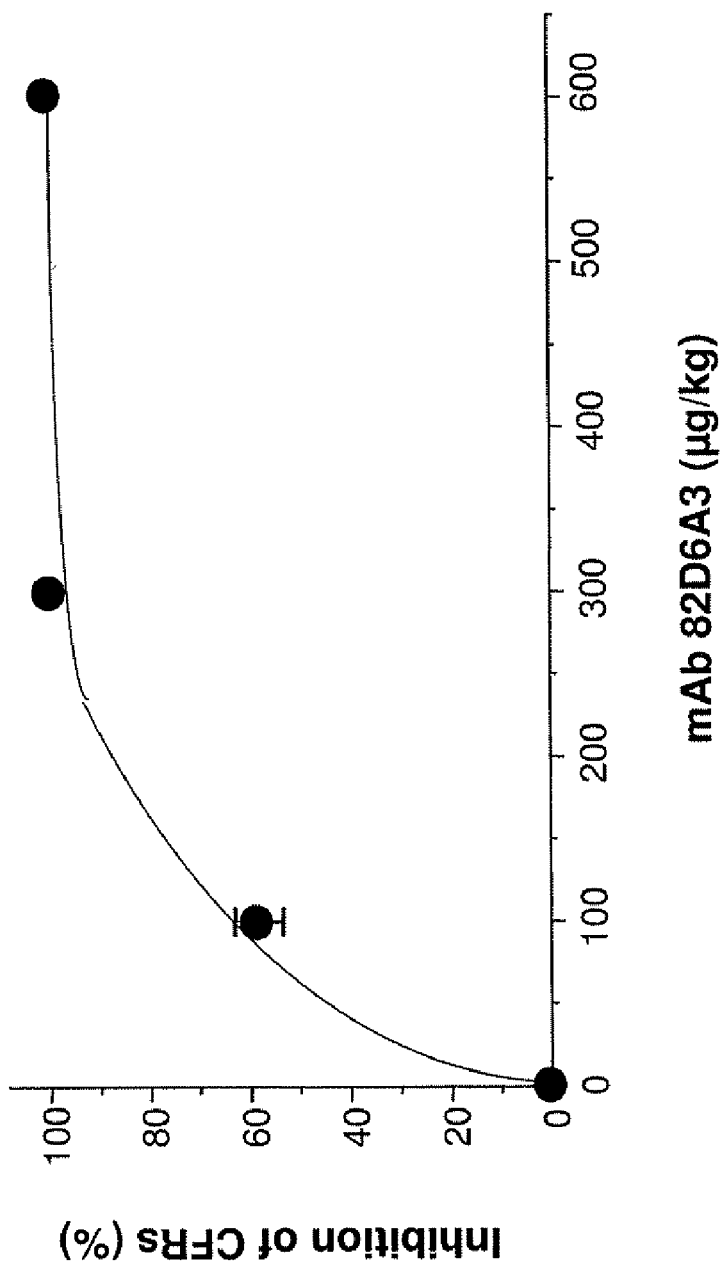

The frequency of the CFRs was not changed by injection of saline (107±7%). A dose of 100 µg/kg mAb 82D6A3 resulted in a significant reduction of the CFRs by 58.3±4.8% (FIG. 1). From a dose of 300 µg/kg onwards the CFRs were completely abolished, and could not be restored by increasing intimal damage or increasing stenosis (FIG. 2).

Platelet Count, Coagulation and Bleeding Time

The platelet count was not significantly affected by injection of the different doses of mAb 82D6A3 (Table I). No significant changes of PT or aPTT were observed in any of the animals (data not shown). The bleeding time was slightly prolonged after injection of 300 µg/kg and 600 µg/kg mAb 82D6A3, but returned to baseline levels 5 hours later (Table I).

Ex Vivo mAb 82D6A3 Plasma Concentration, vWF-Ag Levels, vWF-Occupancy and vWF-Collagen Binding Plasma samples, taken after several time points (see Material and Methods) in each study, were analyzed for mAb 82D6A3 plasma levels, vWF-Ag levels, vWF-occupancy and collagen binding activity ex vivo.

Thirty minutes after injection of the different doses of mAb 821$)_6$A3, a small decrease in vWF-Ag levels were observed, whereas an increase in vWF-Ag levels above baseline was consistently measured after 24 h (Table II & III).

Measurement of the mAb 82D6A3 plasma levels revealed no decrease in mAb 82D6A3 plasma levels in the first 3 hours of the experiment. Then 69%, 23%, 7.6% mAb 82D6A3 was present after 300 min, 24 h and 48 h respectively when 300 µg/kg mAb 82D6A3 was administered (Table II).

Injection of 100 µg/kg mAb 82D6A3 resulted in an ex vivo inhibition of the vWF-collagen binding of 31% (blood sample taken after 1 hour) (Table II). At doses of 300 µg/kg and 600 µg/kg no interaction between baboon vWF and collagen was observed in samples taken up to 5 hours after the administration of the mAb. Blood samples taken 24 hours after the injection of the drug revealed a recovery of the vWF-collagen interaction (Table II).

At 300 min after administration vWF-occupancy was 80% for the 100 µg/kg dosis and near 100% for the 300 µg/kg and 600 µg/kg doses. vWF remained occupied for a long time: even 48 h after the injection of mAb 82D6A3, still 63% of the vWF was occupied with mAb 82D6A3 (Table II).

Figure 3:
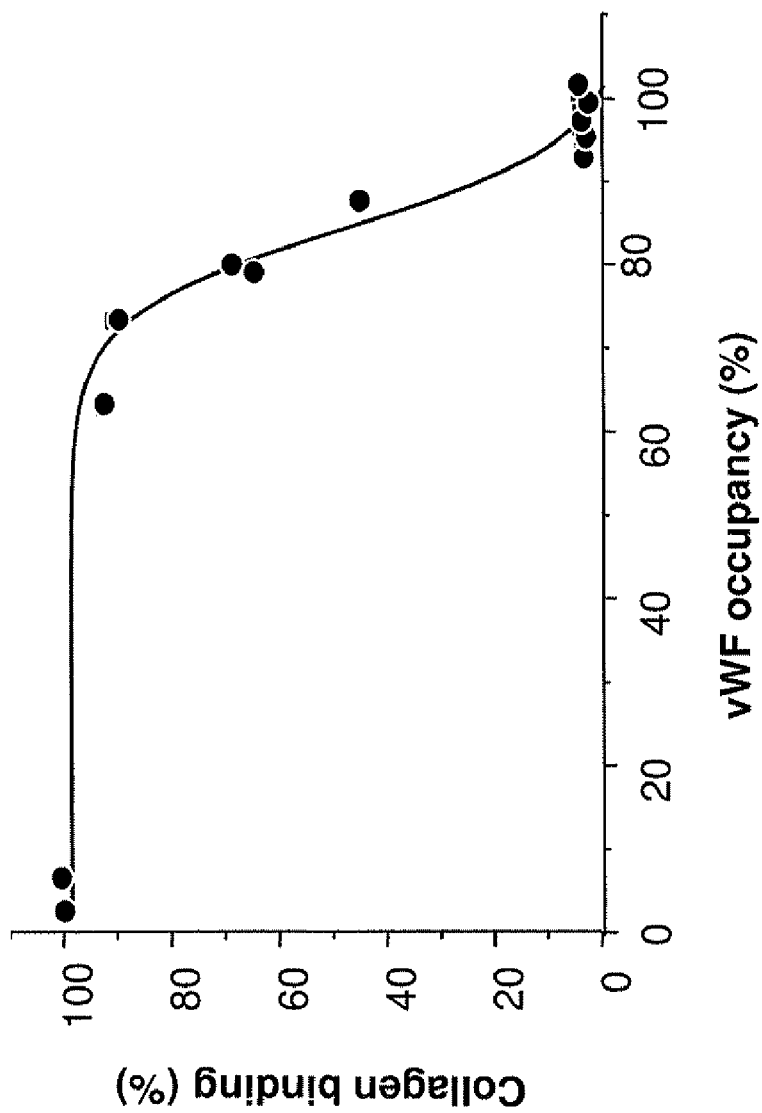

Relation Between the Ex Vivo vWF-Occupancy and Collagen Binding, the vWF-Occupancy and 82D6A3 Plasma Levels and Between vWF-Ag and 82D6A3 Plasma Levels vWF-occupancy inversely correlated with vWF-binding to collagen: to obtain inhibition of vWF-binding to collagen, a vWF occupancy of at least 70% was required, with complete inhibition at 90-100% occupancy (FIG. 3). These data were confirmed by in vitro experiments, where different concentrations of mAb 82D6A3 were added to baboon plasma (FIG. 4): occupancy levels of up to 60% resulted in little inhibition of the vWF binding to collagen, while inhibition was observed when 70%-100% of the vWF-binding sites for the antibody were occupied.

Figure 5:
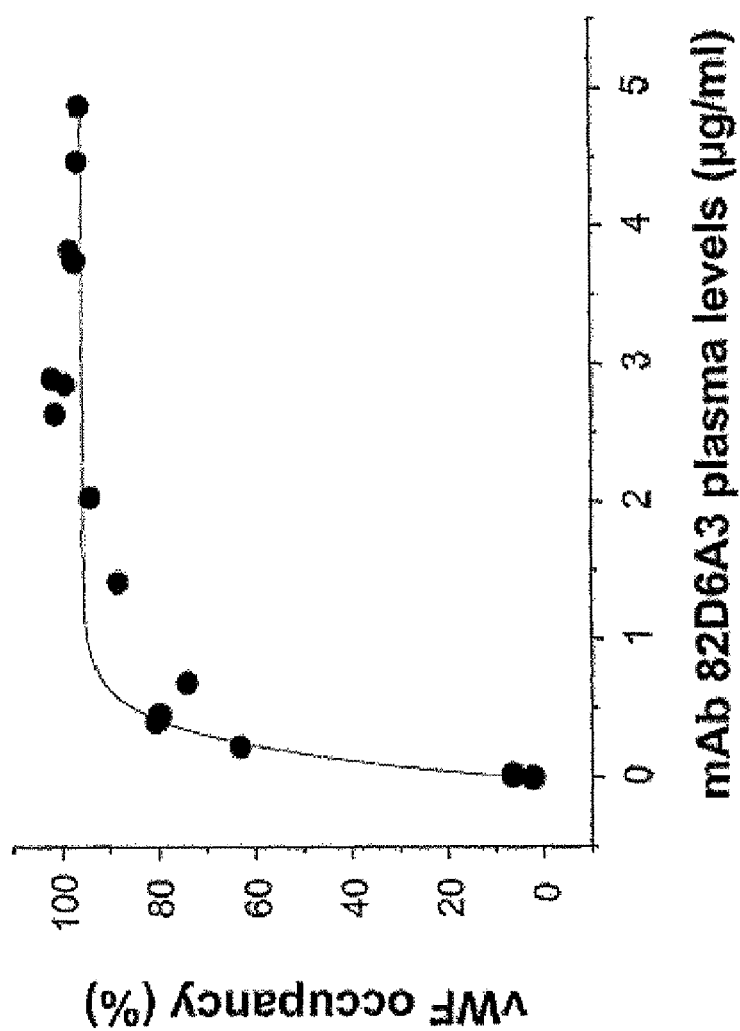

A good relation between 82D6A3 plasma levels and vWF-occupancy was also obtained with a maximum vWF-occupancy from about 1 µg/ml 82D6A3 onwards (FIG. 5).

Characterization of 82D6A3 and its F(ab)-Fragment Both Under Static and Flow Conditions.

Figure 6:
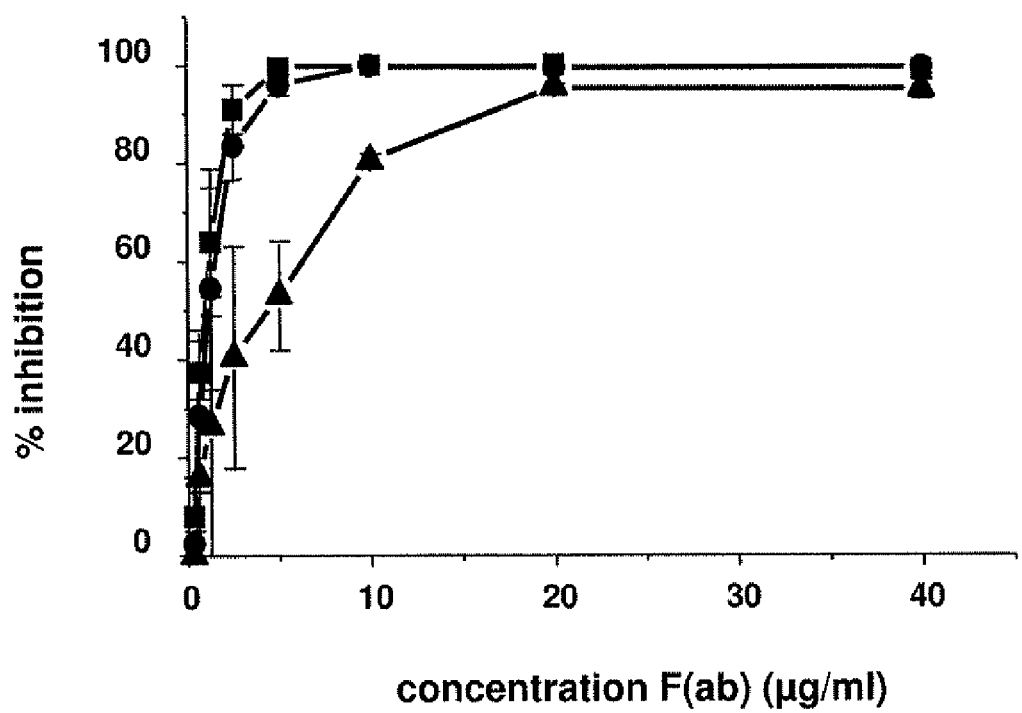

82D6A3 is an anti-vWF antibody that binds with high affinity to vWF (Kd: 0.4 nM) (30) to the SpI proteolytic fragment and the recombinant vWF-A3 domain. Both the MoAb and its F(ab) fragment are able to inhibit plasma or purified vWF-binding to human collagen type I in a specific and dose-dependent manner with an $IC_{50}$ of 20 ng/ml for the MoAb and 1 µg/ml for the F(ab) fragment (FIG. 6). The vWF binding to human collagen type III and calfskin collagen type I was inhibited in the same way. Next; 82D6A3 and its F(ab) fragment were tested under flow conditions at different shear rates (600, 1300 and 2600 $s^{-1}$). At a shear rate of 1300 $s^{-1}$, both the intact MoAb and F(ab) completely inhibited platelet deposition at 1-5 µg/ml and 10 µg/ml resp. (FIG. 7a) and the inhibitory effect increases with the shear applied (FIG. 7b).

Epitope Mapping of 82D6A3 by Means of Phage Display.

2 peptide phage display libraries, a linear pentadecamer and a cyclic hexamer, were used. After three rounds of biopanning with the pentadecamer library individual clones were grown and tested for their ability to bind to 82D6A3 (FIG. 8a). To determine whether the phages were binding to the antigen-binding pocket of the antibody, binding phage-clones were subjected to a competition ELISA to test whether vWF and the A3 domain were able to compete with the phages for binding to the 82D6A3 (FIG. 8b). From the different inhibitory clones that were thus identified, the sequence was determined, which resulted in the identification of 2 sequences: GDCFFGFLNSPWRVC (L15G8) (Seq. Id. 2) and RSSYWVYSPWRFISR (L15C5) (Seq. Id. 3). Both sequences shared the same 4 aa sequence SPWR (Seq. Id. 8). However the affinity of the L15G8 phage for binding to the MoAb was higher than that of the L15C5 phage.

After four rounds of biopanning with the cyclic hexamer library, individual clones were checked for binding to 82D6A3 (FIG. 9a) and for inhibition by vWF and the A3 domain (FIG. 9b). From the phage-clones that did compete ssDNA was prepared and the sequence determined. 8 out of 13 clones displayed CMTSPWRC(C6H5) (Seq. Id. 4), 4 out of 13 CRTSPWRC(C6G12) (Seq. Id. 5) and 1 had the CYRSPWRC(C6A12) (Seq. Id. 6) sequence. These sequences can be aligned with the L15 sequences that also contained the SPWR (Seq. Id. 8) sequence. The L15G8 and C6H5 phage did compete with each other for binding to 82D6A3 (FIG. 10), which let us conclude that the epitope SPWR (Seq. Id. 8) may be part of the epitope of 82D6A3. Furthermore by immunoblotting of the L15G8 and C6H5 phages it was demonstrated that the two cysteins present in both clones are forming a disulfide bridge, necessary for recognition by 82D6A3 (FIG. 11). Both the L15G8 sequence and the C6H5 sequence could be tentatively aligned in the vWF sequence more especially within the A3 domain.

DISCUSSION

Platelet adhesion to a damaged vessel wall is the first step in arterial thrombus formation. The tethering of platelets by vWF to the collagen exposed in the damaged vessel wall is especially important under high shear conditions. Antithrombotic compounds that interfere with the GPIb-vWF axis have been studied in animal models and were shown to be effective (19; 21).

The present study evaluated for the first time the antithrombotic effects of inhibiting the vWF-collagen interaction in vivo. For this purpose, we used a monoclonal anti-human vWF antibody mAb 82D6A3 that by binding to the vWF A3-domain inhibits vWF binding to fibrillar collagens type I and III. mAb 82D6A3 furthermore crossreacts with baboon vWF and inhibits baboon vWF binding to collagen type I under static and flow conditions (Depraetere et al., submitted). A modified Folts' model was used to evaluate the antithrombotic efficacy of mAb 82D6A3 under high shear conditions (25) in baboons. This model allows to study the cyclic flow reductions (CFRs) due to platelet-dependent thrombi forming at the injured, stenotic site of the artery. This cyclic flow model has been described as representing some of the events occurring in patients with unstable angina and useful for studying the mechanisms of unstable angina. This model also allows a reproducible pattern of recurrent thrombosis to be established and is widely accepted as very effective and clinically relevant in testing potential antithrombotic agents (27; 28).

Administration of 100 µg/kg, 300 µg/kg and 600 µg/kg mAb 82D6A3 resulted in 58%, 100% and 100% inhibition of the CFRs respectively (FIG. 2) which corresponded well with the 31%, 96% and 96% (measured in the 60 min plasma samples) ex vivo inhibition of the vWF-collagen interaction (Table II & III).

None of the administered doses, even the highest one, 600 µg/kg, tested, resulted in severe prolongation of the bleeding time or in thrombocytopenia (Table I) nor were the vWF-Ag levels impaired (Table II & III). These results together with the ex vivo inhibition of the vWF-collagen interaction show that the observed inhibitory effect results of a specific inhibition of the vWF-collagen interaction.

The absence of major bleeding problems correlates with out finding that the effect of mAb 82D6A3 on platelet adhesion to human collagen type I was more pronounced at higher shear rates. This confirms that the vWF-collagen interaction is especially important at high shear stress, in other words in the arterial system, which could explain the observation of only a minor prolongation of the bleeding time.

The present invention shows that inhibition of thrombus formation under high shear stress in vivo can not only be obtained by inhibiting the vWF-GPIb interaction but also by interfering with the vWF-collagen interaction. Although also a number of anti-platelet GPIb compounds were successfully used without effect on platelet counts, the risk of inducing thrombocytopenia in some occasions can never be ruled out, as seen with GPIIb-IIIa blockers. A vWF-blocker obviously may be safer in this respect. Both kinds of antithrombotics have the advantage of blocking the first step in thrombus formation which might in addition have some beneficial action in preventing restenosis after PTCA or stenting, in contrast with specific GPIIb-IIIa blockers which only interfere after the platelets have been activated. Activated platelets do not only secrete platelet activating substances but also vasoactive compounds such as platelet derived growth factor, known to induce smooth muscle cell migration and proliferation resulting in restenosis.

It was also revealed that F(ab)-fragments of 82D6A3, directed to the A3-domain of vWF, also bind to vWF with high affinity and are potent inhibitors of the vWF-collagen interaction under both static and flow conditions.

Selection of antibody binding phages from two different phage display libraries, a pentadecamer and cyclic hexamer library, resulted in phages that bind to 82D6A3 in a dose-dependent manner. Moreover, vWF and the recombinant A3-domain were able to inhibit phage binding to the MoAb indicating that the phages bind at or near to the antigen-binding site of 82D6A3. Sequence comparison of the phage displayed peptides revealed that a consensus SPVR (Seq. Id. 8) sequence was present in all phages selected. From these results we can conclude that the SPWR (Seq. Id. 8) sequence may be a part of the 82D6A3 epitope. The SPY (Seq. Id. 8) sequence could be aligned to the VPWN (Seq. Id. 9) sequence (aa 980-983) within the A3 domain, and in the three dimensional structure of the A3-domain located in the vicinity of previously identified amino acid residues important for vWF-collagen interaction. Finding consistently the same 4 aa consensus sequence on the one hand indicates that this sequence really might be important in the antibody recognition In conclusion, the present invention demonstrates that vWF-collagen interaction plays an important role in acute platelet-dependent arterial thrombus formation: blockade of vWF-collagen interaction by mAb 82D6A3 or antigen recognising fragments thereof can induce complete abolition of thrombus formation in the injured and stenosed baboon femoral arteries. Accordingly, the mAb 82D6A3 can be used as a compound for the prevention of acute arterial thrombotic syndromes or to manufacture medicines to prevention of acute arterial thrombotic syndromes.

Legend to Tables

Table I: Platelet Count and Bleeding Time Measured After Administration of Different Doses of mAb 82D6A3 in Baboons.

Values are mean data±$S_D$, /: not determined.

Table II: Ex Vivo mAb 82D6A3 Plasma Concentration, vWF-Ag Levels, vWF-Occupancy and vWF-Collagen Binding Activity Measured After Administration of 100 and 300 µg/kg mAb 82D6A3 to Baboons.

Data are mean data±$S_D$, of n=9 i.e. at each time point, the plasma samples were measured 3 times in three different ELISA's and this for the 3 animal experiments.

Table III: Ex Vivo mAb 82D6A3 Plasma Concentration, vWF-Ag Levels, vWF-Occupancy and vWF-Collagen Binding Activity Measured After Administration of 600 µg/kg mAb 82D6A3.

Data are mean data±$S_D$, of n=6 i.e. at each time point, the plasma samples were 3 times measured in three different ELISA's and this for the 2 animal experiments.

LEGEND TO FIGURES

FIG. 1: Inhibition of CFR by mAb 82D6A3.

Representative records of CFRs showing the effect of a bolus injection of 100 µg/kg and 300 µg/kg mAb 82D6A3.

FIG. 2: Inhibition of CFRs by mAb 82D6A3.

Different dosis of mAb 82D6A3 were administrated to baboons and the CFRs were measured for 60 min. Data represent the mean±$S_D$ with n=3 for 0.1 and 0.3 mg/kg mAb 82D6A3 and n=2 for 0.6 mg/kg.

FIG. 3: Relation between the ex vivo vWF-binding to collagen and vWF-occupancy

All mean data measured at the different time points in the three different dose studies were used (Table II and III).

Figure 4:
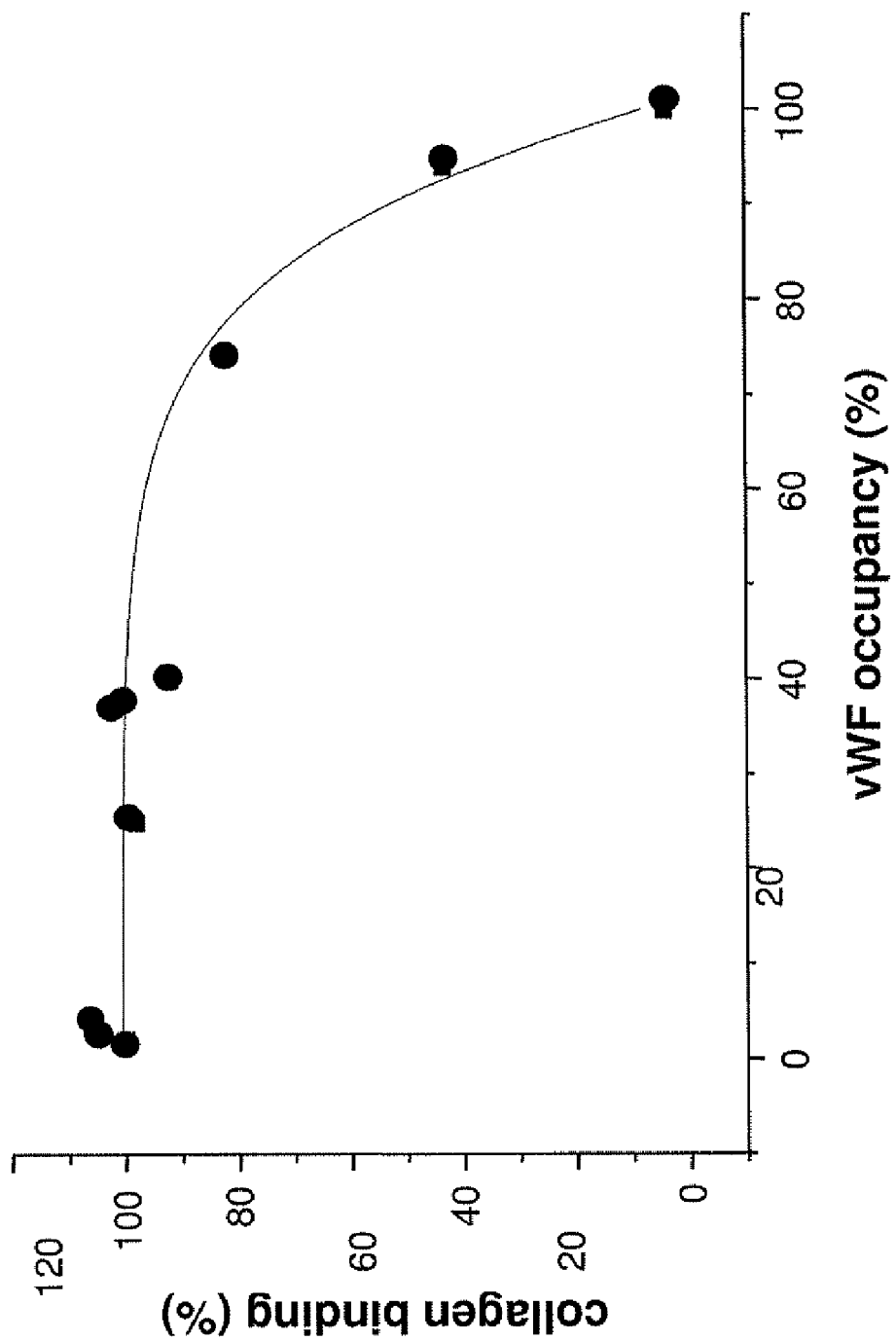

FIG. 4: Correlation between the in vitro measurements of the vWF-binding to collagen and vWF-occupancy The experiment is a representative of 2 experiments, FIG. 5: Relation between the ex vivo vWF-occupancy and mAb 82D6A3 plasma levels.

All mean data measured at the different time points in the three different dosis studies were used (Table II and III).

FIG. 6: Inhibition of vWF binding to human collagen type I

Inhibition of vWF (final concentration 0.5 µg/ml) binding to human collagen type I (□), type III (•) or to calf skin collagen (Δ) by 82D6A3 F(ab). Plates were coated with 25 µg/ml, 100 µl/well collagen. Bound vWF was detected.

Figure 7:
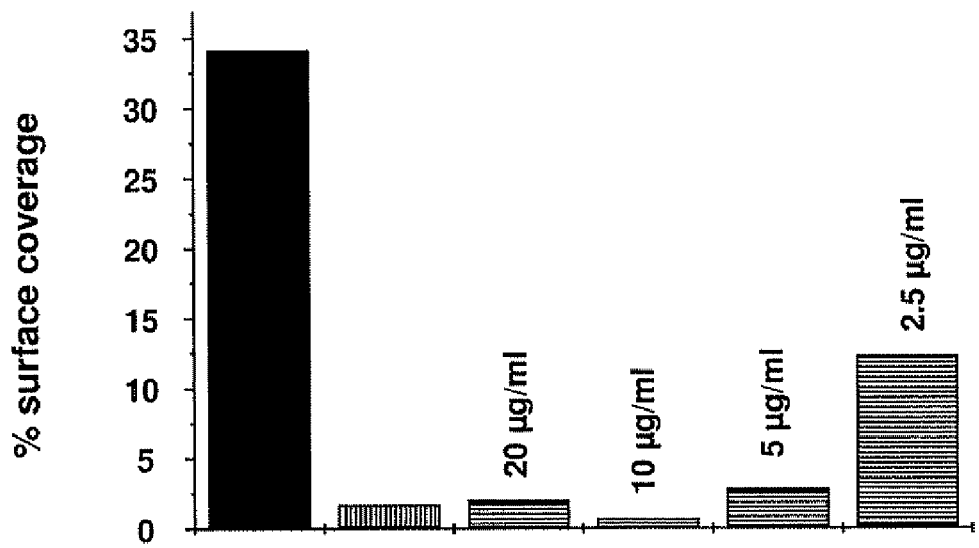
Figure 7:
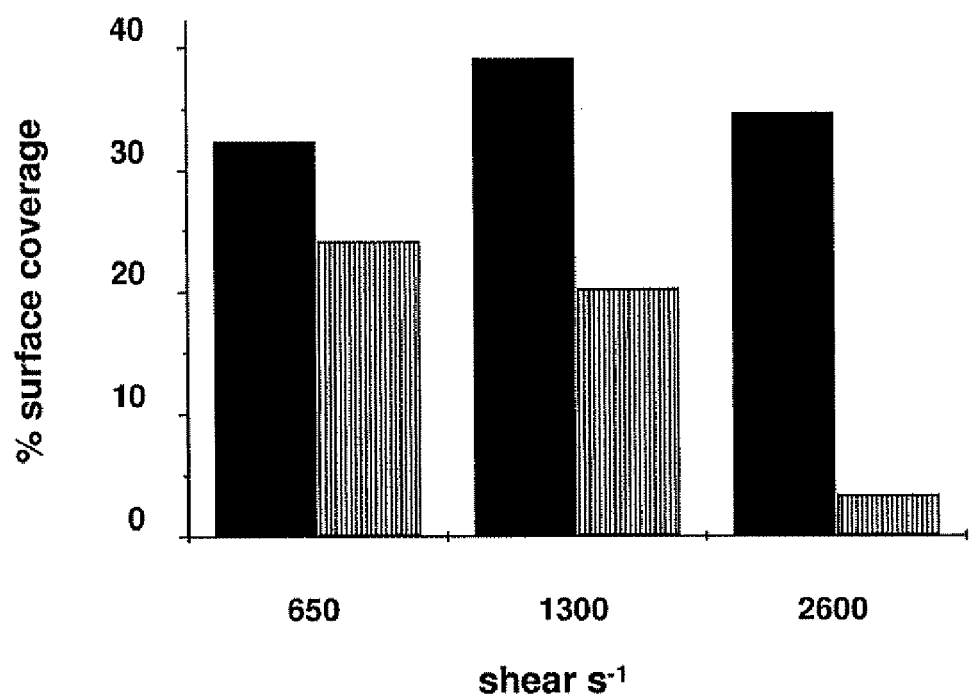

FIG. 7 Inhibition of platelet deposition onto a human collagen type I

FIG. 7b: Inhibition of platelet deposition onto a human collagen type I coated surface in flow at a shear rate 2600 $s^{-s}$. Filled bar: no antibody, open bar: 3 µg/ml 82D6A3, hatched bars: different concentrations of 82D6A3 F(ab)-fragments.

FIG. 7b: Shear-dependent inhibition of platelet deposition onto a human collagen type I coated surface by 82D6A3: filled bars: no antibody, open bars: 5 µg/ml 82D6A3 F(ab)-fragments.

Figure 8:
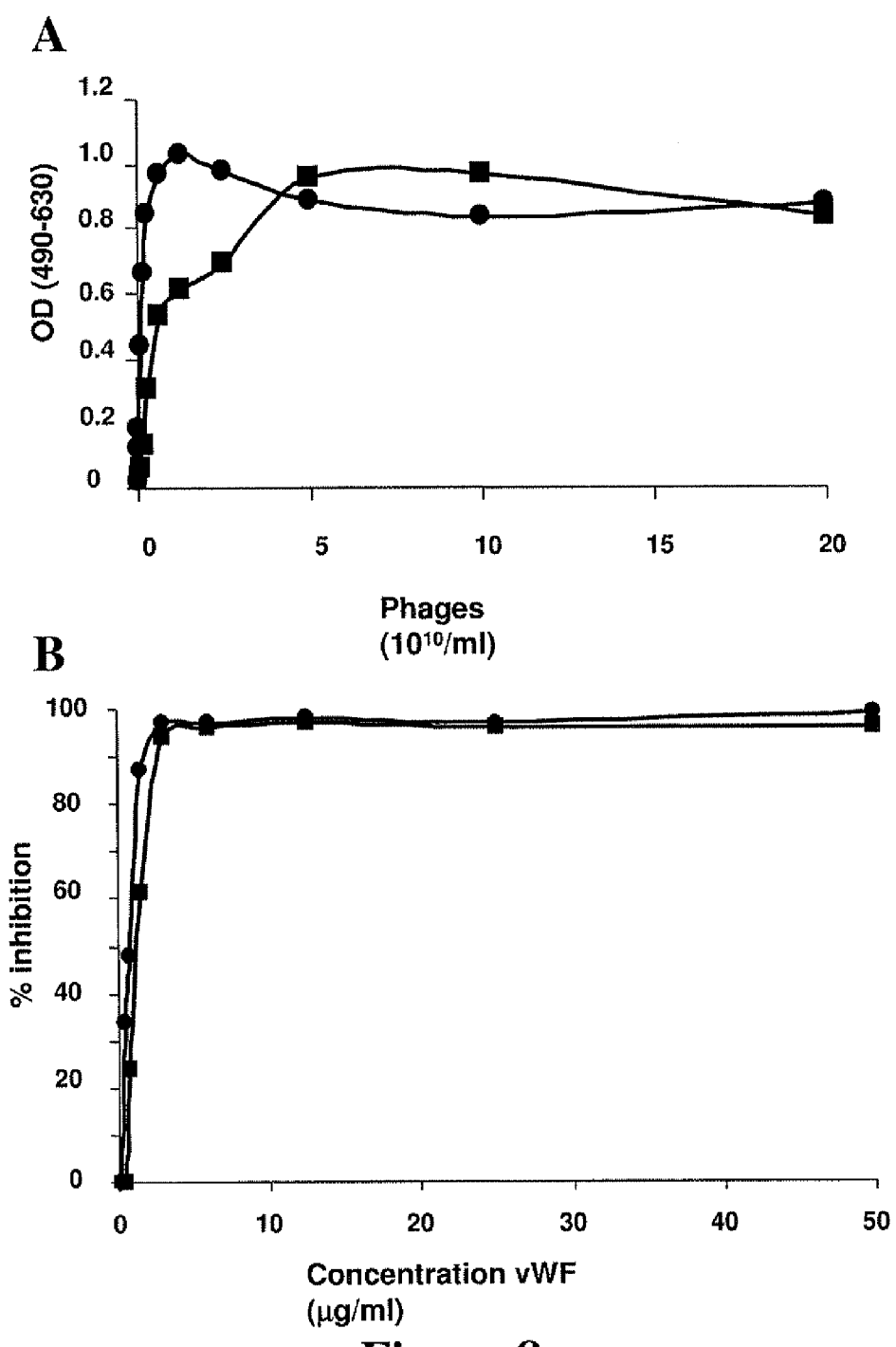

FIG. 8 Binding of phage clones

FIG. 5a: Binding of phage clones L15G8 ( ) and L15C5 ( ) to microtiterplates coated with 10 µg/ml 82D6A3.

FIG. 8b: Inhibition of the binding of phages L 15G8 ( ) and L 15C5 ( ) to microtiterplates coated with 10 µg/ml 82D6A3 by vWF. Final concentration L15G8: $2.10^9$/ml, L15C5: $8.10^9$/ml. Bound phages were detected.

Figure 9:
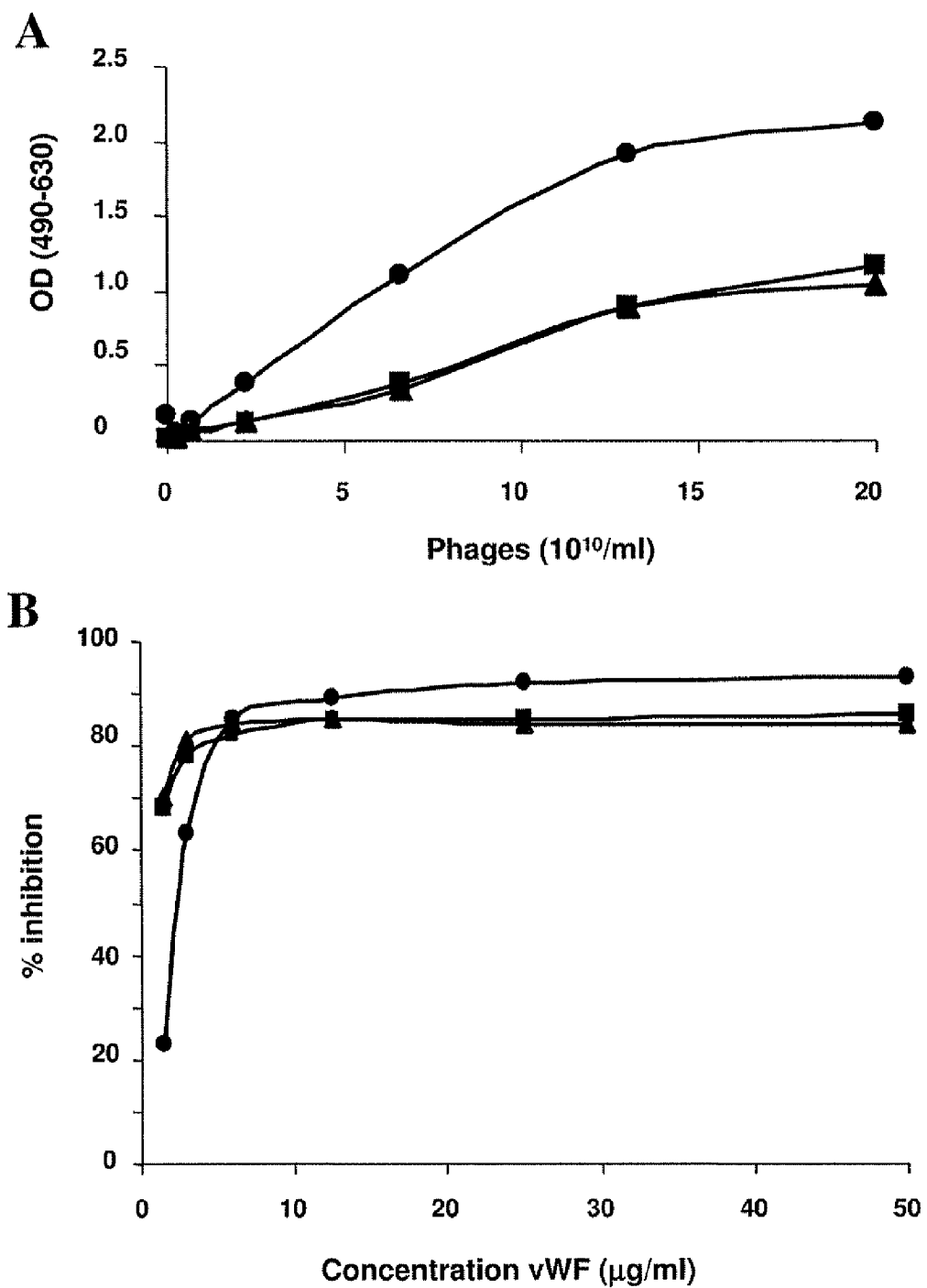

FIG. 9 Binding of phage clones

FIG. 9a: Binding of phage clones C6H5 ( ), C6G12 ( ) and C6A12 ( ) to microtiterplates coated with 10 µg/ml 82D6A3.

FIG. 9b: Inhibition of the binding of phages C6H5 ( ), C6G12 ( ) and C6A12 ( ) to microtiterplates coated with 10 µg/ml MoAb $821)_6$A3 by vWF. Final concentration of phages: $5.10^{10}$/ml. Bound phages were detected.

Figure 10:
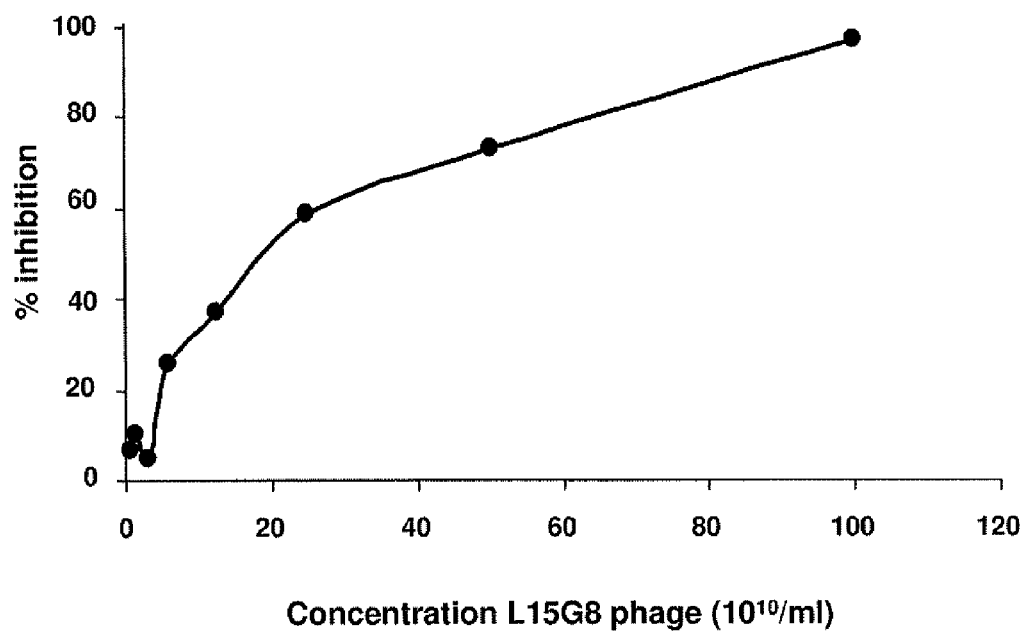

FIG. 10: Inhibition of the binding of biotinylated C6H5-phages to microtiter plates coated with 10 µg/ml 82D6A3 by L15G8 phages Inhibition of the binding of biotiniylated C6H5-phages to microtiter plates coated with 10 µg/ml 82D6A3 by L15G8 phages. C6H5-phages were used at a final concentration of $2.10^{10}$/ml. Bound biotinylated C6H5-phages were detected with streptavidin-HRP.

FIG. 11: Alignment of the vWF sequence with the phage sequences

Alignment of the vWF sequence with the phage sequences (: similarity, | identity).

TABLE 1

| Dose | 100 µg/kg (n = 3) | | 300 µg/kg (n = 3) | | 600 µg/kg (n = 2) | |
|---|---|---|---|---|---|---|
| | Platelet count ($10^3/\mu l$) | Bleeding time (min) | Platelet count ($10^3/\mu l$) | Bleeding time (min) | Platelet count ($10^3/\mu l$) | Bleeding time (min) |
| min | | | | | | |
| 0 | 286 ± 54 | 2.7 ± 0.4 | 286 ± 54 | 2.7 ± 0.4 | 335 | 1.8 |
| 30 | 292 ± 65 | 2.7 ± 0.4 | 265 ± 41 | 4.6 ± 0.6 | 320 | 3.5 |
| 60 | 289 ± 49 | 3.5 ± 2.1 | 287 ± 53 | 7.3 ± 2.5 | 313 | 5.5 |
| 150 | / | / | 309 ± 83 | 6.4 ± 3.1 | 356 | 5 |
| 300 | / | / | 282 ± 7 | 3.15 ± 1.2 | 334 | 3 |
| 24 h | / | / | 312 ± 46 | 3.25 ± 0.3 | 347 | / |
| 48 h | / | / | 306 ± 79 | 3 | / | / |

TABLE 2

| | vWF-Ag levels (µg/ml) | | MoAb 82D6A3 levels (µg/ml) | | vWF occupancy (%) | | collagen binding (%) | |
|---|---|---|---|---|---|---|---|---|
| | 100 µg/kg | 300 µg/kg | 100 µg/kg | 300 µg/kg | 100 µg/kg | 300 µg/kg | 100 µg/kg | 300 µg/kg |
| min | | | | | | | | |
| 0 | 10.2 ± 1.7 | 10.2 ± 1.7 | 0 | 0 | 2.3 ± 1.3 | 2.3 ± 1.3 | 101 ± 7 | 101 ± 7 |
| 30 | 10.2 ± 2.5 | 8.8 ± 1.4 | 0.4 ± 0.07 | 2.9 ± 0.3 | 80 ± 10.8 | 102 ± 10.4 | 64 ± 7 | 4 ± 1 |
| 60 | 8.9 ± 1.4 | 9.1 ± 2.4 | 0.4 ± 0.1 | 2.8 ± 0.3 | 80 ± 2.4 | 99 ± 10.6 | 69 ± 9 | 4 ± 1 |
| 150 | | 9.7 ± 2.7 | | 2.6 ± 0.1 | | 101 ± 7.6 | | 4 ± 1 |
| 300 | | 8.8 ± 0.1 | | 2.0 ± 0.5 | | 94 ± 0.9 | | 4 ± 1 |
| 24 h | | 12.8 ± 1.3 | | 0.7 ± 0.2 | | 74 ± 31 | | 91 ± 18 |
| 48 h | | 13.2 ± 0.8 | | 0.2 ± 0.01 | | 63 ± 7.8 | | 93 ± 0 |

TABLE III

| | VWF-Ag levels (µg/ml) | mAb 82D6A3 levels (µg/ml) | vWF occupancy (%) | collagen binding (%) |
|---|---|---|---|---|
| 0 min | 14 ± 1.7 | 0 | 6.9 ± 0.1 | 100 ± 0 |
| 30 min | 11.5 ± 0.9 | 4.5 ± 0.5 | 96 ± 1 | 4 ± 0.2 |
| 60 min | 10.8 ± 0.1 | 4.8 ± 0.7 | 96 ± 0.2 | 3.5 ± 0.2 |
| 150 min | 11.9 ± 1.8 | 3.8 ± 0.5 | 97 ± 4 | 3.52 ± 0.2 |
| 300 min | 10.5 ± 0 | 3.8 ± 0.6 | 97 | 4 |
| 24 h | 22.9 ± 0 | 1.4 ± 0.01 | 88 | 45 |

REFERENCE LIST (1) Folts J D, Schafer A I, Loscalzo J, Willerson J T, Muller J E. A perspective on the potential problems with aspirin as an antithrombotic agent: a comparison of studies in an animal model with clinical trials. J Am Coll Cardiol 1999; 33(2):295-303.

(2) McGhie A I, McNatt S, Ezov N, Cui K, Mower L K, Hagay Y, Buja L M, Garfinkel L I, Gorecki M, Willerson J T. Abolition of cyclic flow variations in stenosed, endothelium-injured coronary arteries in nonhuman primates with a peptide fragment (VCL) derived from human plasma von Willebrand factor-glycoprotein Ib binding domain [see comments]. Circulation 1994; 90(6):2976-2981.

(3) Sixmna J J, Wester J. The hemostatic plug. Semin Hematol 1977; 14(3):265-299.

(4) Kehrel B. Platelet-collagen interactions. Semin Thromb Hemost 1995; 21(2):123-129.

(5) Phillips D R, Charo I F, Scarborough R M. GPIIb-IIIa: the responsive integrin. Cell 1991; 65(3):359-362.

(6) Tcheng J E. Platelet glycoprotein IIb/IIIa integrin blockade: recent clinical trials in interventional cardiology. Thromb Haemost 1997; 78(1):205-209.

(7) Hanson S R, Sakariassen K S. Blood flow and antithrombotic drug effects. Am Heart J 1998; 135(5 Pt 2 Su):S132-S145.

(8) Coller B S. GPIIb/IIIa antagonists: pathophysiologic and therapeutic insights from studies of c7E3 Fab. Thromb Haemost 1997; 78(1):730-735.

(9) Du X, Beutler L, Ruan C, Castaldi P A, Berndt M C. Glycoprotein Ib and glycoprotein IX are fully complexed in the intact platelet membrane. Blood 1987; 69(5):1524-1527.

(10) Modderman P W, Admiraal L G, Sonnenberg A, dem Borne A E. Glycoproteins V and Ib-IX form a noncovalent complex in the platelet membrane. J Biol Chem 1992; 267(1):364-369.

(11) Vicente V, Kostel P J, Ruggeri Z M. Isolation and functional characterization of the von Willebrand factor-binding domain located between residues His1-Arg293 of the alpha-chain of glycoprotein Ib. J Biol Chem 1988; 263 (34):18473-18479.

(12) Berndt M C, Ward C M, Booth W I, Castaldi P A, Mazurov A V, Andrews R K. Identification of aspartic acid 514 through glutamic acid 542 as a glycoprotein Ib-IX complex receptor recognition sequence in von Willebrand factor. Mechanism of modulation of von Willebrand factor by ristocetin and botrocetin. Biochemistry 1992; 31(45): 11144-11151.

(13) Pareti F I, Niiya K, McPherson J M, Ruggeri Z M. Isolation and characterization of two domains of human von Willebrand factor that interact with fibrillar collagen types I and III. J Biol Chem 1987; 262(28):13835-13841.

(14) Lankhof H, van Hoeij M, Schiphorst M E, Bracke M, Wu Y P, Ijsseldijk M J, Vink T, de Groot P G, Sixma J J. A3 domain is essential for interaction of von Willebrand factor with collagen type III. Thromb Haemost 1996; 75(6):950-958.

(15) Peng M, Lu W, Beviglia L, Niewiarowski S, Kirby E P. Echicetin: a snake venom protein that inhibits binding of von Willebrand factor and alboaggregins to platelet glycoprotein Ib. Blood 1993; 81(9):2321-2328.

(16) Chang M C, Lin H K, Peng H C, Huang T F. Antithrombotic effect of crotalin, a platelet membrane glycoprotein Ib antagonist from venom of Crotalus atrox. Blood 1998; 91(5):1582-1589.

(17) Miller J L, Thiam-Cisse M, Drouet L O. Reduction in thrombus formation by PG-1 F(ab')2, an anti-guinea pig platelet glycoprotein Ib monoclonal antibody. Arterioscler Thromb 1991; 11(5):1231-1236.

(18) Dascombe W H, Hong C, Garrett K O, White J G, Lyle V A, Miller J L, Johnson P C. Artificial microvascular graft thrombosis: the consequences of platelet membrane glycoprotein Ib inhibition and thrombin inhibition. Blood 1993; 82(1):126-134.

(19) Cauwenberghs N, Meiring M, Vauterin S, van W, V, Lamprecht S, Roodt J P, Novak L, Harsfalvi J, Deckmyn H, Kotze H F. Antithrombotic effect of platelet glycoprotein Ib-blocking monoclonal antibody Fab fragments in nonhuman primates. Arterioscler Thromb Vasc Biol 2000; 20(5): 1347-1353.

(20) Cadroy Y, Hanson S R, Kelly A B, Marzec U M, Evatt B L, Kunicki T J, Montgomery R, Harker L A. Relative antithrombotic effects of monoclonal antibodies targeting different platelet glycoprotein-adhesive molecule interactions in nonhuman primates. Blood 1994; 83(11):3218-3224.

(21) Yamamoto H, Vreys I, Stassen J M, Yoshimoto R, Vermylen J, Hoylaerts M F. Antagonism of vWF inhibits both injury induced arterial and venous thrombosis in the hamster. Thromb Haemost 1998; 79(1):202-210.

(22) Golino P, Ragni M, Cirillo P, Pascucci I, Elzekowitz M D, Pawashe A, Scognamiglio A, Pace L, Guarino A, Chiariello M. Aurintricarboxylic acid reduces platelet deposition in stenosed and endothelially injured rabbit carotid arteries more effectively than other antiplatelet interventions. Thromb Haemost 1995; 74(3):974-979.

(23) Zahger D, Fishbein M C, Garfinkel L I, Shah P K, Forrester J S, Regnstrom J, Yano J, Cercek B. VCL, an antagonist of the platelet GP1b receptor, markedly inhibits platelet adhesion and intimal thickening after balloon injury in the rat. Circulation 1995; 92(5):1269-1273.

(24) Hoylaerts M F, Yamamoto H, Nuyts K, Vreys I, Deckmyn H, Vermylen J. von Willebrand factor binds to native collagen VI primarily via its A1 domain. Biochem J 1997; 324 (Pt 1):185-191.

(25) Folts J. An in vivo model of experimental arterial stenosis, intimal damage, and periodic thrombosis. Circulation 1991; 83(6 Suppl):IV3-14.

(26) Vanhoorelbeke K, Cauwenberghs N, Vauterin S, Schlammadinger A, Mazurier C, Deckmyn H. A reliable and reproducible ELISA method to measure ristocetin cofactor activity of von Willebrand factor. Thromb Haemost 2000; 83(1):107-113.

(27) Ikeda H, Koga Y, Kuwano K, Nakayama H, Ueno T, Yoshida N, Adachi K, Park I S, Toshima H. Cyclic flow variations in a conscious dog model of coronary artery stenosis and endothelial injury correlate with acute ischemic heart disease syndromes in humans. J Am Coll Cardiol 1993; 21(4):1008-1017.

(28) Willerson S T, Yao S K, McNatt J, Benedict C R, Anderson H V, Golino P, Murphree S S, Buja L M. Frequency and severity of cyclic flow alternations and platelet aggregation predict the severity of neointimal proliferation following experimental coronary stenosis and endothelial injury. Proc Natl Acad Sci USA 1991; 88(23): 10624-10628.

(29) Harsfalvi J, Stassen J M, Hoylaerts N W, Van Houtte F, Sawyer R T, Vermylen J, Deckmyn H. Calin from Hirudo medicinalis, an inhibitor of von Willebrand factor binding to collagen under static and flow conditions. Blood 1995; 85:705-711.

(30) Hoylaerts N E, Yamamoto H, Nuyts K, Vreys I, Deckmyn H, Vermylen J. von Willebrand factor binds to native collagen VI primarily via its A1 domain. Biochem J 1997; 324 :185-191.

What is claimed is:

1. A method of antithrombotic therapy in an individual, comprising administering to the individual at risk of thrombosis, a therapeutically effective amount of a ligand which is an antibody or an antigen recognizing fragment thereof binding specifically to the A3 domain of von Willebrand Factor (vWF) or an epitope thereof.

2. The method according to claim 1, wherein said ligand binds specifically to an epitope comprising amino acids located within the sequence spanning amino acids 974 to 989 within the A3 domain of vWF corresponding to SEQ ID NO:7.

3. The method according to claim 1, wherein said ligand binds to an epitope comprising amino acids PW (aa981-982) within the A3 domain of vWF corresponding to amino acids 8 and 9 of SEQ ID NO:7.

4. The method according to claim 1, wherein said ligand binds to an epitope comprising amino acids S, P, W and R (SEQ ID NO: 8) within the A3 domain of vWF.

5. The method according to claim 1, wherein said ligand does not block GPIIb-IIIa receptor binding.

6. The method according to claim 1, wherein said therapeutically effective amount inhibits vWF binding to collagen at least up to 5 hours after injection.

7. The method according to claim 1, wherein, at a concentration of 1 μg/ml said ligand completely inhibits platelet deposition on a collagen substrate at a shear rate of 1300 s-1 or higher.

8. The method according to claim 1, wherein said ligand does not induce severe bleeding disorders at a minimal medicinal effective dose to exhibit said antithrombotic action.

9. The method according to claim 1, wherein said ligand, when administered to an individual as an antithrombotic agent, maintains circulating vWF-levels or platelet counts at a minimal medicinal dose effective to exhibit antithrombotic action.

10. The method according to claim 1, wherein said ligand is a monoclonal antibody, deposited with the Belgian Collections of Micro-organisms, under accession number LMBP 5606CB or an antigen recognizing fragment thereof.

11. The method according to claim 1, wherein said treatment maintains the patency of diseased arteries of said patient.

12. The method according to claim 1, wherein said patient is at risk of arterial thrombus formation.

13. The method according to claim 1, wherein said patient is at risk of an occlusive thrombus formation.

14. The method according to claim 1, wherein said patient is at risk of non-occlusive thrombus formation.

15. The method according to claim 1, wherein said patient is at risk of acute coronary occlusion.

16. The method according to claim 1, wherein said patient is at risk of restenosis.

17. The method according to claim 1, wherein said patient is at risk of hyperplasia after agioplasty, atherectomy or arterial stenting.

18. The method according to claim 1, wherein said patient is at risk of unstable angina.

19. The method according to claim 1, which further comprises, administering simultaneously or sequentially to said individual, a thrombolytic agent.

20. The method according to claim 1, wherein said antigen recognizing fragment of said antibody is an Fab, Fab', F(ab')2.

21. The method according to claim 1, wherein said antibody is a humanized antibody having only the hypervariable regions of non-human origin.

* * * * *

UNITED STATES PATENT AND TRADEMARK OFFICE
CERTIFICATE OF CORRECTION

| | | |
|---|---|---|
| PATENT NO. | : 7,754,215 B2 | Page 1 of 1 |
| APPLICATION NO. | : 11/612257 | |
| DATED | : July 13, 2010 | |
| INVENTOR(S) | : Deckmyn et al. | |

It is certified that error appears in the above-identified patent and that said Letters Patent is hereby corrected as shown below:

Title Page, under OTHER PUBLICATIONS, in Mohri et al., replace
"*Bood*" with --*Blood*--;

In Schaffer et al., replace "Thombosis" with --Thrombosis--.

Title Page, under ABSTRACT, replace "medicines to for the" with
--medicines for the--.

Column 2, Lines 13-14, replace "as a medicaments" with
--as a medicament--;

Lines 22-23, replace "invention are do not directly block" with
--invention do not directly block--.

Column 4, Lines 9-10, replace "Partial Tbromboplastin Time" with
--Partial Thromboplastin Time--.

Column 10, Lines 46-47, replace "with out" with --without--.

Column 20, Claim 17, Line 47, replace "agioplasty" with
--angioplasty--.

Signed and Sealed this
Twenty-fifth Day of September, 2012

David J. Kappos
*Director of the United States Patent and Trademark Office*

SEQUENCE LISTING

```
<160> NUMBER OF SEQ ID NOS: 10

<210> SEQ ID NO 1
<211> LENGTH: 18
<212> TYPE: DNA
<213> ORGANISM: Artificial Sequence
<220> FEATURE:
<223> OTHER INFORMATION: Synthetic

<400> SEQUENCE: 1
tgaattttct gtatgagg                                              18

<210> SEQ ID NO 2
<211> LENGTH: 16
<212> TYPE: PRT
<213> ORGANISM: Artificial Sequence
<220> FEATURE:
<223> OTHER INFORMATION: Synthetic

<400> SEQUENCE: 2

Gly Asp Cys Phe Phe Gly Phe Leu Leu Asn Ser Pro Trp Arg Val Cys
```

```
                1               5                  10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic

<400> SEQUENCE: 3

Arg Ser Ser Tyr Trp Val Tyr Ser Pro Trp Arg Phe Ile Ser Arg
 1               5                  10                  15

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Cys Met Thr Ser Pro Trp Arg Cys
 1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

Cys Arg Thr Ser Pro Trp Arg Cys
 1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Cys Tyr Arg Ser Pro Trp Arg Cys
 1               5

<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

Ser Ile Thr Thr Ile Asp Val Pro Trp Asn Val Val Pro Glu Lys
 1               5                  10                  15

<210> SEQ ID NO 8
<211> LENGTH: 4
<212> TYPE: PRT
<213> ORGANISM: Artificial Sequence
<220> FEATURE:
<223> OTHER INFORMATION: Synthetic

<400> SEQUENCE: 8

Ser Pro Trp Arg
 1
```

```
<210> SEQ ID NO 9
<211> LENGTH: 4
<212> TYPE: PRT
<213> ORGANISM: Artificial Sequence
<220> FEATURE:
<223> OTHER INFORMATION: Synthetic

<400> SEQUENCE: 9

Val Pro Trp Asn
 1

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Phe Leu Asn Ser Pro Trp Arg Val
 1               5
```